US008163526B2

(12) United States Patent
Walmsley et al.

(10) Patent No.: US 8,163,526 B2
(45) Date of Patent: Apr. 24, 2012

(54) ETHANOL PRODUCTION

(75) Inventors: Adrian Robert Walmsley, Stockton-on-Tees (GB); Maria Ines Borges-Walmsley, Stockton-on-Tees (GB); Jung Woo Yang, Stockton-on-Tees (GB)

(73) Assignee: The University of Durham, Durham (GB)

( * ) Notice: Subject to any disclaimer, the term of this patent is extended or adjusted under 35 U.S.C. 154(b) by 46 days.

(21) Appl. No.: 12/446,139

(22) PCT Filed: Oct. 17, 2007

(86) PCT No.: PCT/GB2007/003955
§ 371 (c)(1), (2), (4) Date: Apr. 17, 2009

(87) PCT Pub. No.: WO2008/047113
PCT Pub. Date: Apr. 24, 2008

(65) Prior Publication Data
US 2011/0053236 A1    Mar. 3, 2011

(30) Foreign Application Priority Data

Oct. 18, 2006 (GB) .................................. 0620715.3

(51) Int. Cl.
*C12P 7/06* (2006.01)
*C12N 1/20* (2006.01)
(52) U.S. Cl. .................................. 435/161; 435/252.4
(58) Field of Classification Search .................. 435/161, 435/252.4
See application file for complete search history.

(56) References Cited

U.S. PATENT DOCUMENTS

| 5,843,760 A | 12/1998 | Zhang et al. | |
| 6,942,986 B2 * | 9/2005 | Bassler et al. | ............... 435/7.32 |
| 2002/0107364 A1 | 8/2002 | Bassler et al. | |

FOREIGN PATENT DOCUMENTS

| WO | WO 00/32152 | 6/2000 |
| WO | WO 02/094188 | 11/2002 |

OTHER PUBLICATIONS

Palha et al., Ethanol stimulates the flocculation of *Zymomonas mobilis*. Biotechnol. Lett., 1997, vol. 19 (6): 499-501.*
Seo et al., The genome sequence of the ethanologenic bacterium *Zymomonas mobilis* ZM4. Nat. Biotechnol., 2005, vol. 23 (1): 63-68.*
Tano et al., Effect of the presence of initial ethanol on erthanol production in sugar cane juice fermented by *Zymomonas mobilis*. Braz. J. Microbiol., 2003, vol. 34: 242-244.*
Winzer et al., LuxS: its role in central metabolism and the in vitro synthesis of 4-hydroxy-5-methyl-3(2H)-furanone. Microbiol., 2002, vol. 148 : 909-922.*
Communication Pursuant to Article 94(3) EPC for European Application No. 07 824 205.4, issued Sep. 21, 2009.
Search Report for Application No. GB0620715.3, mailed Feb. 20, 2007.
Chen et al., "Structural Identification of a Bacterial Quorum-Sensing Signal Containing Boron," *Nature* 415:545-549, 2002.
Communication Pursuant to Article 94(3) EPC for European Patent Application No. 07 824 205.4 dated May 17, 2010.
Communication Pursuant to Article 94(3) EPC for European Patent Application No. 07 824 205.4 dated Dec. 15, 2010.
Gosset, "Improvement of *Escherichia coli* Production Strains by Modification of the Phosphoenolpyruvate:sugar Phosphotransferase System," *Microbial Cell Factories* 4:14 (2005).
Jeffries, "Ethanol Fermentation on the Move," *Nature Biotechnology* 23(1):40-41 (2005).
Kuipers et al., "Quorum Sensing-Controlled Gene Expression in Lactic Acid Bacteria," *Journal of Biotechnology* 64:15-21 (1998).
Lara et al., "Transcriptional and Metabolic Response of Recombinant *Escherichia coli* to Spatial Dissolved Oxygen Tension Gradients Simulated in a Scale-Down System," *Biotechnology and Bioengineering* 93(2):372-385 (2006).
Sun et al., "Is Autoinducer-2 a Universal Signal of Interspecies Communication: A Comparative Genomic and Phylogenetic Analysis of the Synthesis and Signal Transduction Pathways," *BMC Evolutionary Biology* 4:36 (2004).
International Preliminary Report on Patentability for PCT/GB2007/003955, issued Apr. 22, 2009.
International Search Report for PCT/GB2007/003955, mailed Jun. 2, 2008.
Chiang et al., "S-Adenosylmethionine and Methylation," *FASEB J.* 10: 471-480, 1996.
Loomis and Durst, "Chemistry and Biology of Boron," *Biofactors* 3: 229-239, 1992.
Miller et al., "*Salmonella typhimurium* Recognizes a Chemically Distinct Form of the Bacterial Quorum-Sensing Signal AI-2," *Molecular Cell* 15: 677-687, 2004.
Pappas et al., "Chemical Communication in Proteobacteria: Biochemical and Structural Studies of Signal Synthases and Receptors Required for Intercellular Signalling," *Mol. Microbiol.* 53: 755-769, 2004.
Schauder and Bassler, "The Languages of Bacteria," *Genes Dev.* 15: 1468-1480, 2001.
Schauder et al., "The LuxS Family of Bacterial Autoinducers: Biosynthesis of a Novel Quorum-Sensing Signal Molecule," *Mol. Microbiol.* 41: 463-476, 2001.
Surette et al., "Quorum Sensing in *Escherichia coli*, *Salmonella typhimurium*, and *Vibrio harveyi*: A New Family of Genes Responsible for Autoinducer Production," *Proc. Natl. Acad. Sci. USA.* 96: 1639-1644, 1999.
Winzer et al., "LuxS; Its Role in Central Metabolism and the in Vitro Synthesis of 4-Hydroxy-5-Methyl-3(2H)-Furanone," *Microbiology* 148: 909-922, 2002. Xavier and Bassler, "LuxS Quorum Sensing: More Than Just a Numbers Game," *Curr. Opin. Microbiol.* 6: 191-197, 2003.
Xavier and Bassler, "Interference With AI-2-Mediated Bacterial Cell-Cell Communication," *Nature* 437: 750-753, 2005.

\* cited by examiner

*Primary Examiner* — Ganapathirama Raghu
(74) *Attorney, Agent, or Firm* — Clark & Elbing LLP

(57) ABSTRACT

A method for increasing production of ethanol in an ethanologenic cell using an autoinducer molecule, for example, AI-2.

12 Claims, 7 Drawing Sheets

Figure 4

SEQ ID NO: 1

ATGCCGTTGTTAGATAGCTTCACAGTCGATCATACCCGGATGGAAGCGCCTGCAGTTCGG
GTGGCGAAAACAATGAACACCCCGCATGGCGACGCAATCACCGTGTTCGATCTGCGCTTC
TGCGTGCCGAACAAAGAAGTGATGCCAGAAAGAGGGATCCATACCCTGGAGCACCTGTTT
GCTGGTTTTATGCGTAACCATCTTAACGGTAATGGTGTAGAGATTATCGATATCTCGCCA
ATGGGCTGCCGCACCGGTTTTTATATGAGTCTGATTGGTACGCCAGATGAGCAGCGTGTT
GCTGATGCCTGGAAAGCGGCAATGGAAGACGTGCTGAAAGTGCAGGATCAGAATCAGATC
CCGGAACTGAACGTCTACCAGTGTGGCACTTACCAGATGCACTCGTTGCAGGAAGCGCAG
GATATTGCGCGTAGCATTCTGGAACGTGACGTACGCATCAACAGCAACGAAGAACTGGCA
CTGCCGAAAGAGAAGTTGCAGGAACTGCACATCTAG

Figure 5

SEQ ID NO: 2

```
  1 mplldsftvd htrmeapavr vaktmntphg daitvfdlrf cvpnkevmpe rgihtlehlf
 61 agfmrnhlng ngveiidisp mgcrtgfyms ligtpdeqrv adawkaamed vlkvqdqnqi
121 pelnvyqcgt yqmhslqeaq diarsilerd vrinsneela lpkeklqelh i
```

Figure 6

SEQ ID NO: 3

```
  1 atgaaaatcg gcatcattgg tgcaatggaa gaagaagtta cgctgctgcg tgacaaaatc
 61 gaaaaccgtc aaactatcag tctcggcggt tgcgaaatct ataccggcca actgaatgga
121 accgaggttg cgcttctgaa atcgggcatc ggtaaagtcg ctgcggcgct gggtgccact
181 ttgctgttgg aacactgcaa gccagatgtg attattaaca ccggttctgc cggtggcctg
241 gcaccaacgt tgaaagtggg cgatatcgtt gtctcggacg aagcacgtta tcacgacgcg
301 gatgtcacgg catttggtta tgaatacggt cagttaccag gctgtccggc aggctttaaa
361 gctgacgata aactgatcgc tgccgctgag gcctgcattg ccgaactgaa tcttaacgct
421 gtacgtggcc tgattgttag cggcgacgct ttcatcaacg gttctgttgg tctggcgaaa
481 atccgccaca acttcccaca ggccattgct gtagagatgg aagcgacggc aatcgcccat
541 gtctgccaca atttcaacgt cccgtttgtt gtcgtacgcg ccatctccga cgtggccgat
601 caacagtctc atcttagctt cgatgagttc ctggctgttg ccgctaaaca gtccagcctg
661 atggttgagt cactggtgca gaaacttgca catggctaa
```

Figure 7

SEQ ID NO: 4

MKIGIIGAMEEEVTLLRDKIENRQTISLGGCEIYTGQLNGTEVALLKSGIGKVAAALGATLL
LEHCKPDVIINTGSAGGLAPTLKVGDIVVSDEARYHDADVTAFGYEYGQLPGCPAGFKA
DDKLIAAAEACIAELNLNAVRGLIVSGDAFINGSVGLAKIRHNFPQAIAVEMEATAIAHVCH
NFNVPFVVVRAISDVADQQSHLSFDEFLAVAAKQSSLMVESLVQKLAHG

SEQUENCE LISTING

```
<160> NUMBER OF SEQ ID NOS: 4

<210> SEQ ID NO 1
<211> LENGTH: 516
<212> TYPE: DNA
<213> ORGANISM: Escherichia coli

<400> SEQUENCE: 1
atgccgttgt tagatagctt cacagtcgat catacccgga tggaagcgcc tgcagttcgg      60
gtggcgaaaa caatgaacac cccgcatggc gacgcaatca ccgtgttcga tctgcgcttc     120
tgcgtgccga acaaagaagt gatgccagaa agagggatcc ataccctgga gcacctgttt     180
gctggtttta tgcgtaacca tcttaacggt aatggtgtag agattatcga tatctcgcca     240
atgggctgcc gcaccggttt ttatatgagt ctgattggta cgccagatga gcagcgtgtt     300
gctgatgcct ggaaagcggc aatggaagac gtgctgaaag tgcaggatca gaatcagatc     360
ccggaactga acgtctacca gtgtggcact taccagatgc actcgttgca ggaagcgcag     420
gatattgcgc gtagcattct ggaacgtgac gtacgcatca acagcaacga agaactggca     480
ctgccgaaag agaagttgca ggaactgcac atctag                               516

<210> SEQ ID NO 2
<211> LENGTH: 171
```

<400> SEQUENCE: 2

Met Pro Leu Leu Asp Ser Phe Thr Val Asp His Thr Arg Met Glu Ala
1               5                   10                  15

Pro Ala Val Arg Val Ala Lys Thr Met Asn Thr Pro His Gly Asp Ala
            20                  25                  30

Ile Thr Val Phe Asp Leu Arg Phe Cys Val Pro Asn Lys Glu Val Met
        35                  40                  45

Pro Glu Arg Gly Ile His Thr Leu Glu His Leu Phe Ala Gly Phe Met
    50                  55                  60

Arg Asn His Leu Asn Gly Asn Gly Val Glu Ile Ile Asp Ile Ser Pro
65                  70                  75                  80

Met Gly Cys Arg Thr Gly Phe Tyr Met Ser Leu Ile Gly Thr Pro Asp
                85                  90                  95

Glu Gln Arg Val Ala Asp Ala Trp Lys Ala Ala Met Glu Asp Val Leu
            100                 105                 110

Lys Val Gln Asp Gln Asn Gln Ile Pro Glu Leu Asn Val Tyr Gln Cys
        115                 120                 125

Gly Thr Tyr Gln Met His Ser Leu Gln Glu Ala Gln Asp Ile Ala Arg
    130                 135                 140

Ser Ile Leu Glu Arg Asp Val Arg Ile Asn Ser Asn Glu Glu Leu Ala
145                 150                 155                 160

Leu Pro Lys Glu Lys Leu Gln Glu Leu His Ile
                165                 170

<210> SEQ ID NO 3
<211> LENGTH: 699
<212> TYPE: DNA
<213> ORGANISM: Escherichia coli

<400> SEQUENCE: 3
atgaaaatcg gcatcattgg tgcaatggaa gaagaagtta cgctgctgcg tgacaaaatc      60
gaaaaccgtc aaactatcag tctcggcggt tgcgaaatct ataccggcca actgaatgga     120
accgaggttg cgcttctgaa atcgggcatc ggtaaagtcg ctgcggcgct gggtgccact     180
ttgctgttgg aacactgcaa gccagatgtg attattaaca ccggttctgc cggtggcctg     240
gcaccaacgt tgaaagtggg cgatatcgtt gtctcggacg aagcacgtta tcacgacgcg     300
gatgtcacgg catttggtta tgaataccgg tcagttaccag gctgtccggc aggctttaaa     360
gctgacgata aactgatcgc tgccgctgag gcctgcattg ccgaactgaa tcttaacgct     420
gtacgtggcc tgattgttag cggcgacgct ttcatcaacg ttctgttgg tctggcgaaa     480
atccgccaca acttcccaca ggccattgct gtagagatgg aagcgacggc aatcgcccat     540
gtctgccaca atttcaacgt cccgtttgtt gtcgtacgcg ccatctccga cgtgccgat     600
caacagtctc atcttagctt cgatgagttc ctggctgttg ccgctaaaca gtccagcctg     660
atggttgagt cactggtgca gaaacttgca catggctaa                            699

<210> SEQ ID NO 4
<211> LENGTH: 232
<212> TYPE: PRT
<213> ORGANISM: Escherichia coli

<400> SEQUENCE: 4

Met Lys Ile Gly Ile Ile Gly Ala Met Glu Glu Glu Val Thr Leu Leu
1               5                   10                  15

```
Arg Asp Lys Ile Glu Asn Arg Gln Thr Ile Ser Leu Gly Gly Cys Glu
            20                  25                  30

Ile Tyr Thr Gly Gln Leu Asn Gly Thr Glu Val Ala Leu Leu Lys Ser
        35                  40                  45

Gly Ile Gly Lys Val Ala Ala Ala Leu Gly Ala Thr Leu Leu Leu Glu
    50                  55                  60

His Cys Lys Pro Asp Val Ile Ile Asn Thr Gly Ser Ala Gly Gly Leu
65                      70                  75                  80

Ala Pro Thr Leu Lys Val Gly Asp Ile Val Val Ser Asp Glu Ala Arg
                85                  90                  95

Tyr His Asp Ala Asp Val Thr Ala Phe Gly Tyr Glu Tyr Gly Gln Leu
            100                 105                 110

Pro Gly Cys Pro Ala Gly Phe Lys Ala Asp Asp Lys Leu Ile Ala Ala
        115                 120                 125

Ala Glu Ala Cys Ile Ala Glu Leu Asn Leu Asn Ala Val Arg Gly Leu
    130                 135                 140

Ile Val Ser Gly Asp Ala Phe Ile Asn Gly Ser Val Gly Leu Ala Lys
145                 150                 155                 160

Ile Arg His Asn Phe Pro Gln Ala Ile Ala Val Glu Met Glu Ala Thr
            165                 170                 175

Ala Ile Ala His Val Cys His Asn Phe Asn Val Pro Phe Val Val Val
            180                 185                 190

Arg Ala Ile Ser Asp Val Ala Asp Gln Gln Ser His Leu Ser Phe Asp
        195                 200                 205

Glu Phe Leu Ala Val Ala Ala Lys Gln Ser Ser Leu Met Val Glu Ser
    210                 215                 220

Leu Val Gln Lys Leu Ala His Gly
225                 230
```

ETHANOL PRODUCTION

CROSS-REFERENCE TO RELATED APPLICATIONS

This application claims priority under 35 U.S.C. §371 from international application PCT/GB2007/003955, filed Oct. 17, 2007, which claims priority from Great Britain Patent Application No.: 0620715.3, filed Oct. 18, 2006. Both applications are hereby incorporated by reference in their entirety.

The present invention relates to a method for increasing production of ethanol in an ethanologenic cell using an autoinducer molecule. More particularly, the invention relates to a recombinant expression system for producing ethanol.

BACKGROUND

In the face of escalating oil prices and the growing environmental concerns over the use and depletion of non-renewable energy resources, there is a growing desire to reduce this dependency, stimulating interest in the use of fermentation processes for the large-scale production of alternative biofuels such as ethanol (Editorial (July, 2006) Bioethanol needs biotech now. Nat Biotechnol. 24, 725, Gray, K A et al. (2006) Bioethanol. Cur. Opin. Chem. Biol. 10, 141-6). As a fuel, ethanol is mainly of interest as a petrol additive, or substitute, because ethanol-blended fuel produces a cleaner, more complete combustion that reduces green-house gas and toxic emissions. The production of ethanol in the US has increased from less than 800 million liters in 1980 to about 19 billion liters in 2006, but there are plans to boost production to more than 36 billion liters by 2012. In 2004 this industry added U$14 billions to the US Gross Domestic Product (Securing America's energy future (2006), brochure produced by the Renewable Fuels Association). However, the US is not the largest producer of bioethanol, this occurs in Brazil. Recently, Brazil and the UK have agreed to co-operate in the development of facilities for bioethanol production in other countries, such as South Africa.

As a consequence of the surge in demand for biofuels, ethanol-producing microorganisms, such as the Gram-negative bacterium *Zymomonas mobilis*, are of considerable interest due to their potential for the production of bioethanol (Jeffries, T W (2005) Ethanol fermentation on the move. Nat Biotechnol. 23, 40-1). *Z. mobilis* attracted attention early in the development of ethanol fuel technology because it grows and ferments rapidly, and has a product rate and yield significantly higher than that of yeast. Furthermore, it tolerates high levels of ethanol, a virtually unique property among bacteria, and sugars. It is distinctive in that it uses the Entner-Doudoroff (E-D) pathway for glucose metabolism rather than the more familiar glycolytic pathway used by most bacteria and yeast. The key enzyme of the E-D pathway is pyruvate decarboxylase (PDC), which is only rarely found in bacteria. Unlike glycolysis, which can theoretically generate two moles of ATP for each mole of glucose fermented to ethanol, the E-D pathway has a net yield of only one ATP per mole of glucose. This low yield of ATP results in low cell mass and allows higher ethanol yields. Although wild-type strains of *Z. mobilis* can only use glucose, fructose and sucrose as carbon substrates, recent research has focused on the development of recombinant strains capable of converting cheaper lignocellulosic hydrolysates to ethanol. All in, these features of *Z. mobilis* have made it an attractive candidate for bioethanol production (Seo, J-S et al. (2005) The genome sequence of the ethanologenic bacterium *Zymomonas mobilis* ZM4. Nat Biotechnol. 23, 63-8).

To keep in step with the growing demand for biofuels will require the engineering of new strains of fermentative microorganisms that can produce these more efficiently; and to enable the engineering of such strains will require more detailed information on the genetic circuits involved in regulating biofuel production.

U.S. Pat. No. 5,514,583 discloses a transformed *Z. mobilis* xylose fermenting strain (CP4/pZB4 and pZB5) having exogenous genes, and plasmid vectors (pZB4 and pZB5) encoding xylose isomerase, xylulokinase, transaldolase and transketolase, and further comprising at least one promoter (Pgap and Peno) recognized by *Zymomonas* which regulates the expression of at least one of said genes. The microorganism is capable of growing on xylose as a sole carbon source, and fermenting xylose to ethanol at about 88% of the maximum theoretic yield.

U.S. Pat. Nos. 5,712,133 and 5,726,053 relates to, inter alia, *Z. mobilis* arabinose fermenting transformants (39676/pZB 206), containing exogenous genes that encode L-arabinose isomerase, L-ribulokinase and L-ribulose-5-phosphate-4-epimerase, transaldolase and transketolase which impart arabinose to ethanol fermentation capability. The plasmid vector (pZB 206) and a process of using the transformants of the fermentation of a glucose and arabinose containing substrate is also described.

U.S. Pat. No. 5,843,760 discloses a *Z. mobilis* xylose and arabinose fermenting transformant (206C/pZB301) containing exogenous genes encoding xylose isomerase, xylulokinase, L-arabinose isomerase, L-ribulokinase, L-ribulose-5-phosphate 4-epimerase, transaldolase and transketolase, and further comprising at least one promoter recognized by *Zymomonas* which regulates the expression of at least one of said genes, wherein said microorganism is capable of growing on arabinose and/or xylose, alone or in combination, as the carbon source and fermenting said arabinose and xylose to ethanol. The process of using the transformants together with the plasmid vectors (pZB301, pZB401, pZB402, and pZB 403) is also described.

We have established that the production of bioethanol by *Z. mobilis* is regulated by the quorum sensing (QS) molecule AI-2 (Bassler B L et al. (1997) Cross-species induction of luminescence in the quorum-sensing bacterium *Vibrio harveyi*. J. Bacteriol. 179, 40-3, Chen, X et al. (2002) Structural identification of a bacterial quorum-sensing signal containing boron. Nature 415, 545-9). The use of AI-2 to enhance bioethanol production is likely to be a better tactic than simply engineering bacteria, since one can expect that the expression of all the genes necessary for enhancing production will be regulated in a coordinated manner, whilst also activating mechanisms to increase the tolerance of the bacterium to the increased levels of ethanol.

BRIEF SUMMARY OF THE DISCLOSURE

In a first aspect the invention provides a method for increasing production of ethanol in an ethanologenic cell comprising culturing the ethanologenic cell in the presence of an autoinducer molecule.

In a second aspect the invention provides use of an autoinducer molecule in a method for producing ethanol using an ethanol producing bacterial cell.

In a third aspect the invention provides an ethanologenic cell transfected with a first nucleic acid encoding at least one polypeptide which on expression results in the cell producing an autoinducer molecule which when sensed by the cell increases the cells production of ethanol compared to a non-transfected cell.

In a fourth aspect the invention provides an ethanologenic cell treated with an autoinducer molecule and which produces ethanol in increased amounts compared to an untreated ethanologenic counterpart.

In a fifth aspect the invention provides a genetically modified ethanologenic cell which produces at least one autoinducer molecule and which exhibits increased ethanol production compared to an unmodified ethanologenic counterpart.

In a sixth aspect the invention provides a method for producing ethanol comprising:
  i) incorporating a first nucleic acid molecule which encodes a polypeptide for the production of an autoinducer molecule into an expression vector for expression in a host cell;
  ii) transfecting an ethanologenic cell with the expression vector
wherein the resulting transfected cell exhibits increased ethanol production compared to an untransformed ethanologenic counterpart.

In a seventh aspect the invention provides a reaction vessel containing an ethanologenic cell according to an aspect of the present invention and medium sufficient to support the growth of said cell.

In an eighth aspect the invention provides a method for producing ethanol comprising:
  i) providing a vessel comprising an ethanologenic cell according to any aspect of the present invention;
  ii) providing the cell with a substrate for enzymatic conversion to an autoinducer molecule;
  iii) providing cell culture conditions which facilitate ethanol production by a cell culture of said ethanologenic cell contained in the vessel; and optionally
  iii) collecting ethanol from the vessel.

In a ninth aspect the invention provides an apparatus for the production and collection of ethanol by a cell comprising:
  i) a reaction vessel containing an ethanologenic cell according any aspect of the present invention; and
  ii) a second vessel in fluid connection with said cell culture vessel wherein said second vessel is adapted for the collection and/or storage of ethanol produced by cells contained in the cell culture vessel in (i).

In a tenth aspect the invention provides Use of a *Zymomonas mobilis* bacterial cell as a recombinant expression system for the production of ethanol, wherein said cell is transformed with a nucleic acid molecule that encodes a polypeptide that converts S-ribosylhomocystine to an autoinducer-2 molecule.

In an eleventh aspect the invention provides use of a LuxS expression construct in a recombinant expression system for the production of ethanol.

In a preferred embodiment wherein said ethanologenic cell is a bacterial cell, more preferably a gram negative bacterial cell. Preferably said bacterial cell is of the genus *Zymomonas* spp, more preferably *Zymomonas mobilis*, still more preferably *Zymomonas mobilis* ZM4.

In a preferred embodiment the ethanologenic cell does not synthesise the autoinducer molecule.

In a preferred embodiment said autoinducer molecule is an autoinducer-2 molecule. Preferably the autoinducer molecule is produced in vitro. Preferably said autoinducer molecule is provided in a culture medium.

Alternatively, said autoinducer molecule is provided by co-culturing the ethanol producing bacterial cell with a autoinducer molecule producing bacterial cell. Preferably, said autoinducer molecule producing bacterial cell is selected from the group consisting of *Vibrio harveyi, Escherichia coli, Helicobactor pylori, Neisseria meningitides, Porphyromonas gingivalis, Streptococcus pyrogenes, Shigella flexneri* and *Salmonella typhimurium*.

In a preferred embodiment the autoinducer molecule is present at the start of culture. Alternatively, the autoinducer molecule is present after the start of culture. Alternatively, the autoinducer molecule is present continuously during culture. Alternatively the autoinducer molecule is present in the log phase of culture.

In a preferred embodiment said first nucleic acid molecule encodes a polypeptide for the conversion of S-ribosylhomocysteine to an autoinducer-2 molecule. Preferably said first nucleic acid molecule is selected from the group consisting of:
  i) a nucleic acid molecule comprising the nucleotide sequence of SEQ ID NO: 1;
  ii) a nucleic acid molecule having at least 60% identity to the nucleotide sequence of SEQ ID NO: 1 and which encodes a polypeptide that has LuxS activity;
  iii) a nucleic acid molecule which hybridizes to the nucleic acid sequence of SEQ ID NO:1 and which encodes a polypeptide that has LuxS activity;
  iv) a nucleic acid molecule comprising a nucleotide sequence that is degenerate as a result of the genetic code to the sequences of i), ii) and iii) above;
  v) a nucleic acid molecule that encodes a polypeptide comprising the amino acid sequence of SEQ ID NO:2; and
  vi) a nucleic acid molecule that encodes a polypeptide having at least 60% identity to the amino acid sequence of SEQ ID NO:2.

More preferably said nucleic acid molecule consists of the nucleotide sequence of SEQ ID NO:1.

Preferably, said ethanologenic cell is transfected with a second nucleic acid molecule that encodes a polypeptide for the conversion of S-adenosylhomocysteine to S-ribosylhomocysteine. Preferably said second nucleic acid molecule is selected from the group consisting of:
  i) a nucleic acid molecule comprising the nucleotide sequence of SEQ ID NO: 3;
  ii) a nucleic acid molecule having at least 60% identity to the nucleotide sequence of SEQ ID NO: 3 and which encodes a polypeptide that has MTA/SAHase activity;
  iii) a nucleic acid molecule which hybridizes to the nucleic acid sequence of SEQ ID NO:3 and which encodes a polypeptide that has MTA/SAHase activity;
  iv) a nucleic acid molecule comprising a nucleotide sequence that is degenerate as a result of the genetic code to the sequences of i), ii) and iii) above;
  v) a nucleic acid molecule that encodes a polypeptide comprising the amino acid sequence of SEQ ID NO:4; and
  vi) a nucleic acid molecule that encodes a polypeptide having at least 60% identity to the amino acid sequence of SEQ ID NO:4.

More preferably said second nucleic acid molecule consists of the nucleotide sequence of SEQ ID NO:3.

In a preferred embodiment said expression vector comprises a transcription promoter element that confers inducible expression on said first nucleic acid molecule. Alternatively said expression vector comprises a transcription promoter element that confers repressible expression on said first nucleic acid molecule. Alternatively, said expression vector comprises a transcription promoter element that confers constitutive expression on said first nucleic acid molecule. Alternatively, said second nucleic acid molecule is incorporated into the expression vector comprising the first nucleic acid molecule.

In a preferred embodiment, said reaction vessel is a bioreactor, more preferably a fermentor.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

BRIEF DESCRIPTION OF THE DRAWINGS

FIG. 4 is the nucleotide sequence of SEQ ID NO:1;
FIG. 5 is the amino acid sequence of SEQ ID NO:2;
FIG. 6 is the nucleotide sequence of SEQ ID NO:3;
FIG. 7 is the amino acid sequence of SEQ ID NO:4;

DETAILED DESCRIPTION

Figure 1:
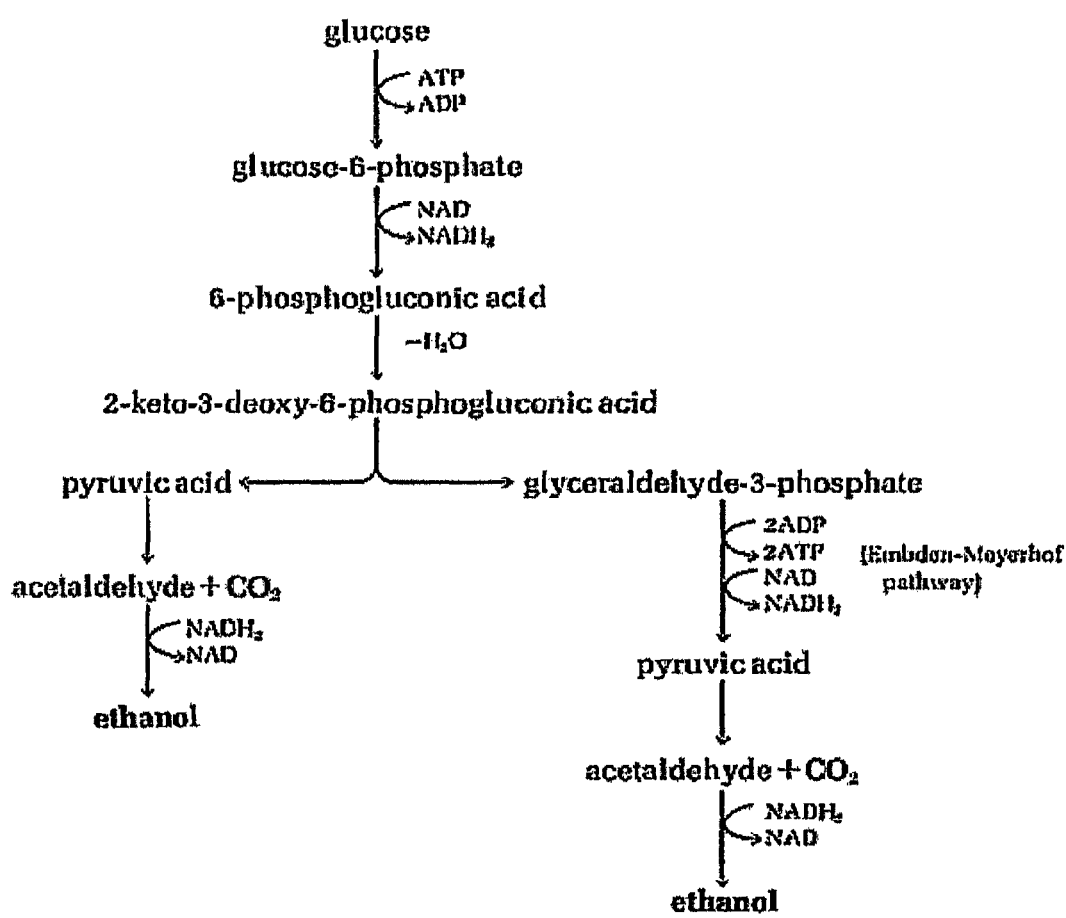
FIG. 1 is a schematic representation of the Entner-Doudoroff (ED) fermentation pathway.

Baterium of the genus *Zymomonas*, employ the Entner-Doudoroff (ED) fermentation pathway, illustrated generally at FIG. 1. The ED pathway produces two ethanol and two $CO_2$ form glucose, with a net energy gain of one mole ATP per molecule of glucose. The pathway requires only two enzymic activities; pyruvate decarboxylase and alcohol dehydrogenase. Pyruvate decarboxylase drives the flow of pyruvate to ethanol. Pyruvate decarboxylase catalyzes the nonoxidative decarboxylation of pyruvate to produce acetaldehyde and carbon dioxide. Two alcohol dehydrogenase isozymes are present in *Zymomonas* and serve to catalyze the reduction of acetaldehyde to ethanol during the fermentation process, accompanied by the oxidation of NADH to NAD+. The key enzyme of the E-D pathway is pyruvate decarboxylase (PDC), which is rarely found in bacteria. Unlike glycolysis, which can theoretically generate two moles of ATP for each mole of glucose fermented to ethanol, the E-D pathway has a net yield of only one ATP per mole of glucose. This low yield of ATP results in low cell mass and allows higher ethanol yields. Although wild-type strains of *Z. mobilis* can only use glucose, fructose and sucrose as carbon substrates, recent research has focused on the development of recombinant strains capable of converting cheaper lignocellulosic hydrolysates to ethanol.

The present invention is based on the surprising finding that the production of bioethanol by *Z. mobilis* is up-regulated in the presence of molecules involved in quorum sensing known as autoinducer molecules. Quorum sensing is the phenomenon by which bacteria communicate.

Quorum sensing autoinducer molecules are secreted chemical signalling molecules produced by bacteria that allow bacteria to communicate. In quorum sensing, bacteria asses their population density and the population density of other types of bacteria by detecting the concentration of a particular quorum sensing autoinducer, which correlates with cell density. This allows bacterial gene expression to be co-ordinated in a multi-cellular fashion (Withers, H., Swift, S. & Williams, P. (2001). *Curr Opin Microbiol* 4, 186-193). Quorum sensing occurs in numerous Gram positive and Gram negative bacteria. A wide variety of multicellular behaviour has been found to be quorum-sensing-controlled, for example bioluminescence, antibiotic biosynthesis, biofilm differentiation, plasmid conjugal transfer, competence for DNA uptake and sporulation. Several families of autoinducers have been identified. N-Acyl-L-homoserine lactones (AHL's) are produced by Gram-negative bacteria through enzymes of the LuxI protein family. AHL molecules have been shown to activate transcriptional regulators of the LuxR family at a critical concentration an have also been shown to act as virulence factors (Gardiner, S. M., Chhabra, S. R., Harty, C., Williams, P., Pritchard, D. I., Bycroft, B. W. & Bennett, T. (2001). *Br J Pharmacol* 133, 1047-1054, Telford, G., Wheeler, D., Williams, P., Tomkins, P. T., Appleby, P., Sewell, H., Stewart, G. S. A. B., Bycroft, B. W. & Pritchard, D. I. (1998) *Infect Immun* 66, 36-42.).

In Gram-positive bacteria post-translationally modified peptides have been shown to act as autoinducers (Kleerebezem, M., Quadri, L. E. N., Kuipers, O. P. & de Vos, W. M. (1997). *Mol Microbiol* 24, 895-904).

A family of autoinducers has been described which is present in both Gram-negative and Gram-positive bacteria (Surette, M. G., Miller, M. B. & Bassler, B. L. (1999) *Proc Natl Acad Sci USA* 96, 1639-1644). Autoinducer-2 (AI-2) is one member of this family. The LuxS protein is required for the production of autoinducer 2 (AI-2), which exerts its activity via a complex phospho-relay system. AI-2 activity has been discovered in many bacteria including *Escherichia coli, Helicobacter pylori, Neisseria meningitidis, Porphyromonas gingivalis, Streptococcus pyogenes, Shigella flexneri* and *Salmonella typhimurium* In addition, highly conserved LuxS homologues have been identified in a large number of pathogenic and non-pathogenic bacteria by database analysis.

AI-2 is produced by the actions of LuxS, the AI-2 synthase from S-adenosylmethionine (SAM) via three enzymatic steps. SAM is used as a methyl donor andseceral SAM-dependent methyl transferases act on SAM to transfer the methyl group from SAM. A by-product of this step is the production of S-adenosyhomocystein (SAH). SAH is degraded by an enzyme called Pfs. Pfs is an MTA/SAHase and catalyzes the formation of S-ribosylhomocysteine (SRH) from S-adenosylhomocysteine (SAH) to release adenine and the production of 5'-methylthioribose (MTR) from 5'-methylthioadenosine (MTA), also releasing adenine (Della Ragione, F., M. Porcelli, M. Carteni-Farina, V. Zappia, and A. E. Pegg. 1985, Biochem. J. 232:335-341, Greene, R. C. 1996. Biosynthesis of methionine, p. 542-560. In F. C. Neidhardt, R. Curtiss III, J. L. Ingraham, E. C. C. Lin, K. B. Low, B. Magasanik, W. S. Reznikoff, M. Riley, M. Schaechter, and H. E. Umbarger (ed.), *Escherichia coli* and *Salmonella*: cellular and molecular biology, 2nd ed., vol. 1. ASM Press, Washington, D.C., Miller, C. H., and J. A. Duerre. 1968. J. Biol. Chem. 243:92-97). SAH and MTA are inhibitors of S-adenosylmethionine (SAM)-requiring reactions, and the accumulation of these metabolites is avoided through the activities of Pfs.

In a final step, SRH is converted to homocystein and 4,5-dihydroxy-2,3-pentanedione by the enzymic action of LuxS. The enzyme Pfs acts directly upstream of LuxS in the AI-2 production pathway and is responsible for generation of adenine and the LuxS substrate SRH from SAH (Schauder, S., K. Shokat, M. G. Surette, and B. L. Bassler. 2001. Mol. Microbiol. 41:463-476).

A recent study by Schauder et al. has shown that purified Pfs and LuxS enzymes are necessary and sufficient for AI-2 production in vitro with SAH as a substrate (Schauder, S., and B. L. Bassler. 2001. The languages of bacteria. Genes Dev. 15:1468-1480).

After its formation by LuxS, 4,5-dihydroxy-2,3-pentanedione spontaneously cyclizes to become a furanone. It has been demonstrated that AI-2 is a five-carbon furanone that results from the spontaneous cyclization of 4,5-dihydroxy-2,3-pentanedione, the product of the LuxS-catalysed cleavage of the ribosyl moiety from SRH (Schauder, S., Shokat, K., Surette, M. G. & Bassler, B. L. (2001). *Mol Microbiol* 41, 463-476). It has therefore been suggested that AI-2 is a furanosyl borate diester (Che. Et al (2002) Nature, 415,545).

In order to stimulate ethanol production, the ethanologenic cell can be supplied directly with AI-2 or modified so as to contain the necessary enzymes (LuxS or LuxS and Pfs) to produce AI-2.

The direct substrate required for the production of AI-2 from LuxS is S-ribosylhomocysteine. In order to express AI-2 a cell will require with a direct source of S-ribosylhomocysteine or a mechanism to produce S-ribosylhomocysteine, e.g. the Pfs polypeptide and its substrate S-adenosyhomocystein.

An ethanologenic cell or expression vector of the present invention can therefore include the LuxS coding sequence illustrated in FIG. 4 and encoding the polypeptide of FIG. 5, or the LuxS coding sequence and the Pfs coding sequence illustrated in FIG. 6 encoding the Pfs polypeptide illustrated in FIG. 7.

If the cell is transfected with just the LuxS coding sequence, the cell will require a direct source of S-ribosylhomocysteine in order to produce AI-2. If the cell is transfected with both the LuxS coding sequence and the Pfs coding sequence, the cell will require S-adenosyhomocystein to produce AI-2. S-adenosyhomocystein is a product of S-Adenosylmethionine metabolism. Accordingly, S-adenosyhomocystein can be provided by direct S-Adenosylmethionine (SAM) metabolism in bacterial cells (Winzer et al, (2002), Microbiol, 148, 909-922).

Vector

As used herein, the term "vector" refers to a nucleic acid molecule capable of transporting another nucleic acid to which it has been linked. The vector can be capable of autonomous replication or it can integrate into a host DNA. The vector may include restriction enzyme sites for insertion of recombinant DNA and may include one or more selectable markers. The vector can be a nucleic acid in the form of a plasmid, a bacteriophage or a cosmid. Most preferably the vector is suitable for bacterial expression, e.g. for expression in *Zymomans* spp, preferably for expression in *Zymomonas mobilis*.

Preferably the vector is capable of propagation in the bacterial cell and is stably transmitted to future generations.

"Operably linked" as used herein, refers to a single or a combination of the above-described control elements together with a coding sequence in a functional relationship with one another, for example, in a linked relationship so as to direct expression of the coding sequence.

"Regulatory sequences" as used herein, refers to, DNA or RNA elements that are capable of controlling gene expression. Examples of expression control sequences include promoters, enhancers, silencers, Shine Dalgarno sequences, TATA-boxes, internal ribosomal entry sites (IRES), attachment sites for transcription factors, transcriptional terminators, polyadenylation sites, RNA transporting signals or sequences important for UV-light mediated gene response. Preferably the expression vector includes one or more regulatory sequences operatively linked to the nucleic acid sequence to be expressed. Regulatory sequences include those which direct constitutive expression, as well as tissue-specific regulatory and/or inducible sequences.

"Promoter", as used herein, refers to the nucleotide sequences in DNA or RNA to which RNA polymerase binds to begin transcription. The promoter may be inducible or constitutively expressed. Alternatively, the promoter is under the control of a repressor or stimulatory protein. Preferably the promoter is a T7, T3, lac, lac UV5, tac, trc, [lambda]PL, Sp6 or a UV-inducible promoter.

"Transcriptional terminator" as used herein, refers to a DNA element, which terminates the function of RNA polymerases responsible for transcribing DNA into RNA. Preferred transcriptional terminators are characterized by a run of T residues preceded by a GC rich dyad symmetrical region.

"Translational control element", as used herein, refers to DNA or RNA elements that control the translation of mRNA. Preferred translational control elements are ribosome binding sites. Preferably, the translational control element is from a homologous system as the promoter, for example a promoter and it's associated ribozyme binding site. Preferred ribosome binding sites are T7 or T3 ribosome binding sites.

"Restriction enzyme recognition site" as used herein, refers to a motif on the DNA recognized by a restriction enzyme.

"Selectable marker" as used herein, refers to proteins that, when expressed in a host cell, confer a phenotype onto the cell which allows a selection of the cell expressing said selectable marker gene. Generally this may be a protein that confers resistance to an antibiotic such as ampicillin, kanamycin, chloramphenicol, tetracyclin, hygromycin, neomycin or methotrexate. Further examples of antibiotics are Penicillins; Ampicillin HCl, Ampicillin Na, Amoxycillin Na, Carbenicillin sodium, Penicillin G, Cephalosporins, Cefotaxim Na, Cefalexin HCl, Vancomycin, Cycloserine. Other examples include Bacteriostatic Inhibitors such as: Chloramphenicol, Erythromycin, Lincomycin, Tetracyclin, Spectinomycin sulfate, Clindamycin HCl, Chlortetracycline HCl.

The design of the expression vector depends on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., the Lux S polypeptide encoded by SEQ ID NO:2 or the MTA/SAHase polypeptide encoded by SEQ ID NO:4).

Expression of proteins in prokaryotes is most often carried out in a bacterial host cell with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such vectors are within the scope of the present invention.

Preferably the vector comprises those genetic elements which are necessary for expression of the LuxS protein in the bacterial cell. The elements required for transcription and translation in the bacterial cell include a promoter, a coding region for the LuxS protein complex, and a transcriptional terminator.

Expression vectors of the invention can be bacterial expression vectors, for example recombinant bacteriophage DNA, plasmid DNA or cosmid DNA, yeast expression vectors e.g. recombinant yeast expression vectors, vectors for expression in insect cells, e.g., recombinant virus expression vectors, for example baculovirus, or vectors for expression in plant cells, e.g. recombinant virus expression vectors such as cauliflower mosaic virus, CaMV, tobacco mosaic virus, TMV, or recombinant plasmid expression vectors such as Ti plasmids.

Preferably, the vector is a bacterial expression vector. Preferably, the expression vector is a high-copy-number expression vector; alternatively, the expression vector is a low—copy-number expression vector, for example, a Mini-F plasmid.

Preferably, is a vector suitable for expression in *Zymomonas* spp, more preferably an RP4, R68 or RSF1010 vector.

AI2 Producing Enzymes

As used herein, the term "nucleic acid molecule" includes DNA molecules (e.g., a cDNA or genomic DNA) and RNA molecules (e.g., a mRNA) and analogs of the DNA or RNA generated, e.g., by the use of nucleotide analogs. The nucleic acid molecule can be single-stranded or double-stranded, but preferably is double-stranded DNA.

With regards to genomic DNA, the term "isolated" includes nucleic acid molecules that are separated from the chromosome with which the genomic DNA is naturally associated. Preferably, an "isolated" nucleic acid is free of sequences that naturally flank the nucleic acid (i.e., sequences located at the 5'- and/or 3'-ends of the nucleic acid) in the genomic DNA of the organism from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under stringent conditions" describes conditions for hybridization and washing. Stringent conditions are known to those skilled in the art and can be found in available references (e.g., Current Protocols in Molecular Biology, John Wiley & Sons, N.Y., 1989, 6.3.1-6.3.6). Aqueous and non-aqueous methods are described in that reference and either can be used. A preferred example of stringent hybridization conditions are hybridization in 6× sodium chloride/sodium citrate (SSC) at about 45° C., followed by one or more washes in 0.2×SSC, 0.1% (w/v) SDS at 50° C. Another example of stringent hybridization conditions are hybridization in 6×SSC at about 45° C., followed by one or more washes in 0.2×SSC, 0.1% (w/v) SDS at 55° C. A further example of stringent hybridization conditions are hybridization in 6×SSC at about 45° C., followed by one or more washes in 0.2×SSC, 0.1% (w/v) SDS at 60° C. Preferably, stringent hybridization conditions are hybridization in 6×SSC at about 45° C., followed by one or more washes in 0.2×SSC, 0.1% (w/v) SDS at 65° C. Particularly preferred stringency conditions (and the conditions that should be used if the practitioner is uncertain about what conditions should be applied to determine if a molecule is within a hybridization limitation of the invention) are 0.5 molar sodium phosphate, 7% (w/v) SDS at 65° C., followed by one or more washes at 0.2×SSC, 1% (w/v) SDS at 65° C. Preferably, an isolated nucleic acid molecule of the invention that hybridizes under stringent conditions to the sequence of SEQ ID NO:1 or 3.

As used herein, a "naturally-occurring" nucleic acid molecule refers to an RNA or DNA molecule having a nucleotide sequence that occurs in nature (e.g., encodes a natural protein).

As used herein, the terms "gene" and "recombinant gene" refer to nucleic acid molecules which include an open reading frame encoding protein, and can further include non-coding regulatory sequences and introns.

A "non-essential" amino acid residue is a residue that can be altered from the wild-type sequence of (e.g., the sequence of SEQ ID NO:2 or 4) without abolishing or, more preferably, without substantially altering a biological activity, whereas an "essential" amino acid residue results in such a change. For example, amino acid residues that are conserved among the polypeptides of the present invention, e.g., those present in the conserved potassium channel domain are predicted to be particularly non-amenable to alteration, except that amino acid residues in transmembrane domains can generally be replaced by other residues having approximately equivalent hydrophobicity without significantly altering activity.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in protein is preferably replaced with another amino acid residue from the same side chain family. Alternatively, in another embodiment, mutations can be introduced randomly along all or part of coding sequences, such as by saturation mutagenesis, and the resultant mutants can be screened for biological activity to identify mutants that retain activity. Following mutagenesis of SEQ ID NO:1 or 3, the encoded proteins can be expressed recombinantly and the activity of the protein can be determined.

As used herein, a "biologically active portion" of protein includes fragment of protein that participate in an interaction between molecules and non-molecules. Biologically active portions of protein include peptides comprising amino acid sequences sufficiently homologous to or derived from the amino acid sequences of the protein, e.g., the amino acid sequences shown in SEQ ID NO: 2 or 4, which include fewer amino acids than the full length protein, and exhibit at least one activity of the encoded protein. Typically, biologically active portions comprise a domain or motif with at least one activity of the protein, e.g., the enzymatically convert S-adenosylhomocystein to S-ribosylhomocystein or enzymatically convert S-ribosylhomocystein to Autoinducer-2.

A biologically active portion of protein can be a polypeptide that is, for example, 50, 100, 150, 200, 250, 300, 350, 400, 450, 500 or more amino acids in length of SEQ ID NO: 3, 5, 8, 10 or 13. Biologically active portions of protein can be used as targets for developing agents that modulate-mediated activities, e.g., biological activities described herein.

Calculations of sequence homology or identity (the terms are used interchangeably herein) between sequences are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 75%, 80%, 82%, 84%, 85%, 86%, 87%, 88%, 89%, 90%, 91%, 92%, 93%, 94%, 95%, 96%, 97%, 98%, 99%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman et al. (1970) *J. Mol. Biol.* 48:444-453) algorithm which has been incorporated into the GAP program in the GCG software package, using either a BLOSUM 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a BLOSUM 62 scoring matrix with a gap penalty of 12, a gap extend penalty of 4, and a frameshift gap penalty of 5.

The percent identity between two amino acid or nucleotide sequences can be determined using the algorithm of Meyers et al. (1989) *CABIOS* 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. MoL Biol.* 215:403-410). BLAST nucleotide searches can be performed with the NBLAST program, score =100, wordlength =12 to obtain nucleotide sequences homologous to nucleic acid molecules of the invention. BLAST protein searches can be performed with the XBLAST program, score =50, wordlength =3 to obtain amino acid sequences homologous to protein molecules of the invention. To obtain gapped alignments for comparison purposes, gapped BLAST can be utilized as described in Altschul et al. (1997, *Nucl. Acids Res.* 25:3389-3402). When using BLAST and gapped BLAST programs, the default parameters of the respective programs (e.g., XBLAST and NBLAST) can be used.

Polypeptides of the present invention can have amino acid sequences sufficiently or substantially identical to the amino acid sequences of SEQ ID NO:2 or 4. The terms "sufficiently identical" or "substantially identical" are used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain or common functional activity. For example, amino acid or nucleotide sequences that contain a common structural domain having at least about 60%, or 65% identity, likely 75% identity, more likely 85%, 90%. 91%, 92%, 93%, 94%, 95%, 96%, 97%, 98% or 99% identity are defined herein as sufficiently or substantially identical.

Preferably expression vectors and ethanologenic cells of the present application comprises a nucleic acid sequence encoding a LuxS protein.

The nucleic acid sequence preferably encodes the LuxS polypeptide from *E.coli*, which is encoded by the nucleic acid of SEQ ID NO:1 and which has the amino acid sequence of SEQ ID NO:2.

The nucleic acid sequence of LuxS is shown in SEQ ID NO: 1. The sequence is approximately 516 nucleotides in length and encodes a 171 amino acid polypeptide designated LuxS (SEQ ID NO:2).

The nucleic acid sequence of Pfs is shown in SEQ ID NO:3. The sequence is approximately 699 nucleotides in length and encodes a 232 amino acid polypeptide designated Pfs (SEQ ID NO:4).

Further nucleic acid molecules incorporated into the expression vectors and ethanologenic cells of the present invention are described below.

In one embodiment, the expression vector or ethanologenic cell of the invention comprises nucleic acid molecule comprising the nucleotide sequence of SEQ ID NO:1, or a portions or fragment thereof. In one embodiment the nucleic acid molecule comprises a nucleotide sequence encoding the polypeptide of SEQ ID NO' 2. In yet another embodiment, the nucleotide sequence comprises fragments of SEQ ID NO:1, preferably the fragments are biologically active fragments, i.e. having LuxS activity.

In another embodiment, the nucleic acid sequence that is the complement of the nucleotide sequences shown in SEQ ID NO:1, or portions or fragments thereof. In other embodiments, the nucleic acid sequence is sufficiently complementary to the nucleotide sequence shown in of SEQ ID NO:1 such that it can hybridize to the nucleotide sequence shown in any of SEQ ID NO:1, thereby forming stable duplexes.

In one embodiment, the nucleic acid sequence is at least about: 60%, 65%, 70%, 75%, 80%, 85%, 90%, 91%, 92%, 93%, 94%, 95%, 96%, 97%, 98%, 99% or 100%, homologous to the entire length of the nucleotide sequence shown in SEQ ID NO:1, or portions or fragments thereof.

In one embodiment the nucleic acid sequence encodes a naturally occurring allelic variant of a polypeptide comprising the amino acid sequence shown in SEQ ID NO: 1. Functional allelic variants will typically contain only conservative substitution of one or more amino acids of SEQ ID NO: 1, or substitution, deletion or insertion of non-critical residues in non-critical regions of the protein. Non-functional allelic variants are naturally occurring amino acid sequence variants of SEQ ID NO: 1 that do not have LuxS activity. Non-functional allelic variants will typically contain a non-conservative substitution, a deletion, or insertion or premature truncation of the amino acid sequence of SEQ ID NO: 1, or a substitution, insertion or deletion in critical residues or critical regions. Nucleic acid molecules corresponding to natural allelic variants and homologues of the LuxS nucleic acid molecules of the invention can be isolated based on their homology to the nucleic acid molecules of the invention using the nucleotide sequences described in SEQ ID NO:1 or a portion thereof, as a hybridization probe under stringent hybridization conditions.

In another embodiment, the nucleic acid molecule comprises a nucleotide sequence that encodes the polypeptide of SEQ ID NO: 2 or portions or fragments thereof. In another embodiment, the nucleic acid molecule comprises a nucleotide sequence that encodes a polypeptide that is at least about: 60%, 65%, 70%, 75%, 80%, 85%, 90%, 91%, 92%, 93%, 94%, 95%, 96%, 97%, 98%, 99% or 100%, homologous to the entire length the polypeptide of SEQ ID NO: 2, or portions or fragments thereof.

In a further embodiment the expression vector or ethanogenic cell additionally comprises a nucleic acid molecule comprising the nucleotide sequence of SEQ ID NO:3, or portions or fragments thereof. In another embodiment, the nucleic acid molecule comprises a nucleotide sequence that is at least about: 60%, 65%, 70%, 75%, 80%, 85%, 90%, 91%, 92%, 93%, 94%, 95%, 96%, 97%, 98%, 99% or 100%, homologous to the entire length of the nucleotide sequence of SEQ ID NO:3, or portions or fragments thereof. In one embodiment the nucleic acid sequence encodes a naturally occurring allelic variant of a polypeptide comprising the amino acid sequence shown in SEQ ID NO: 3. Functional allelic variants will typically contain only conservative substitution of one or more amino acids of SEQ ID NO: 3, or substitution, deletion or insertion of non-critical residues in non-critical regions of the protein. Non-functional allelic variants are naturally occurring amino acid sequence variants of SEQ ID NO: 3 that do not have MTA/SAHase activity. Non-functional allelic variants will typically contain a non-conservative substitution, a deletion, or insertion or premature truncation of the amino acid sequence of SEQ ID NO: 3, or a substitution, insertion or deletion in critical residues or critical regions. Nucleic acid molecules corresponding to natural allelic variants and homologues of the Pfm nucleic acid molecules of the invention can be isolated based on their homology to the nucleic acid molecules of the invention using the nucleotide sequences described in SEQ ID NO:3 or a portion thereof, as a hybridization probe under stringent hybridization conditions.

In another embodiment, the nucleic acid molecule comprises a nucleotide sequence that encodes the polypeptide of SEQ ID NO: 4or portions or fragments thereof. In another embodiment, the nucleic acid molecule comprises a nucleotide sequence that encodes a polypeptide that is at least about: 60%, 65%, 70%, 75%, 80%, 85%, 90%, 91%, 92%, 93%, 94%, 95%, 96%, 97%, 98%, 99% or 100%, homologous to the entire length the polypeptide of SEQ ID NO: 4, or portions or fragments thereof.

In another embodiment any of the nucleic acid molecules described previously, comprises specific changes in the nucleotide sequence so as to optimize codons and mRNA secondary structure for translation in the host cell. Preferably, the codon usage of the nucleic acid is adapted for expression in the host cell, for example codon optimisation can be achieved using Calcgene, Hale, R S and Thomas G. *Protein Exper. Purif.* 12, 185-188 (1998), UpGene, Gao, W et al. *Biotechnol. Prog.* 20, 443-448 (2004), or Codon Optimizer, Fuglsang, A. *Protein Exper. Purif.* 31, 247-249 (2003). Amending the nucleic acid according to the preferred codon optimization can be achieved by a number of different experimental protocols, including, modification of a small number of codons, Vervoort et al. *Nucleic Acids Res.* 25: 2069-2074 (2000), or rewriting a large section of the nucleic acid sequence, for example, up to 1000 by of DNA, Hale, R S and Thomas G. *Protein Exper. Purif.* 12,185-188 (1998). Rewriting of the nucleic acid sequence can be achieved by recursive PCR, where the desired sequence is produced by the extension of overlapping oligonucleotide primers, Prodromou and Pearl, *Protein Eng.* 5: 827-829 (1992). Rewriting of larger stretches of DNA may require up to three consecutive rounds of recursive PCR, Hale, R S and Thomas G. *Protein Exper. Purif.* 12, 185-188 (1998), Te'o et al, *FEMS Microbiol. Lett.* 190: 13-19, (2000).

Alternatively, the level of cogent tRNA can be elevated in the host cell. This elevation can be achieved by increasing the copy number of the respective tRNA gene, for example by inserting into the host cell the relevant tRNA gene on a compatible multiple copy plasmid, or alternatively inserting the tRNA gene into the expression vector itself.

In another embodiment any of the nucleic acid molecule described previously, comprises specific changes in the nucleotide sequence so as to optimize expression, activity or functional life of the LuxS and MTA/SAHase polypeptides. Preferably, the nucleic acids described previously are subjected to genetic manipulation and disruption techniques. Various genetic manipulation and disruption techniques are known in the art including, but not limited to, DNA Shuffling (U.S. Pat. No. 6,132,970, Punnonen J et al, *Science & Medicine*, 7(2): 38-47, (2000), U.S. Pat. No. 6,132,970), serial mutagenesis and screening. One example of mutagenesis is error-prone PCR, whereby mutations are deliberately introduced during PCR through the use of error-prone DNA polymerases and reaction conditions as described in US 2003152944, using for example commercially available kits such as The GeneMorph® II kit (Stratagene®, US). Randomized DNA sequences are cloned into expression vectors and the resulting mutant libraries screened for altered or improved protein activity.

Preparation of LuxS Expression Vectors

A man of skill in the art will be aware of the molecular techniques available for the preparation of expression vectors.

The nucleic acid molecule for incorporation into the expression vector of the invention, as described above, can be prepared by synthesizing nucleic acid molecules using mutually priming oligonucleotides and the nucleic acid sequences described herein.

A number of molecular techniques have been developed to operably link DNA to vectors via complementary cohesive termini. In one embodiment, complementary homopolymer tracts can be added to the nucleic acid molecule to be inserted into the vector DNA. The vector and nucleic acid molecule are then joined by hydrogen bonding between the complementary homopolymeric tails to form recombinant DNA molecules.

In an alternative embodiment, synthetic linkers containing one or more restriction sites provide are used to operably link the nucleic acid molecule to the expression vector. In one embodiment, the nucleic acid molecule is generated by restriction endonuclease digestion as described earlier. Preferably, the nucleic acid molecule is treated with bacteriophage T4 DNA polymerase or *E. coli* DNA polymerase I, enzymes that remove protruding, 3'-single-stranded termini with their 3'-5'-exonucleolytic activities, and fill in recessed 3'-ends with their polymerizing activities, thereby generating blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the product of the reaction is a nucleic acid molecule carrying polymeric linker sequences at its ends. These nucleic acid molecules are then cleaved with the appropriate restriction enzyme and ligated to an expression vector that has been cleaved with an enzyme that produces termini compatible with those of the nucleic acid molecule.

Alternatively, a vector comprising ligation-independent cloning (LIC) sites can be employed. The required PCR amplified nucleic acid molecule can then be cloned into the LIC vector without restriction digest or ligation (Aslanidis and de Jong, *Nucl. Acid. Res.* 18, 6069-6074, (1990), Haun, et al, *Biotechniques* 13, 515-518 (1992).

In order to isolate and/or modify the nucleic acid molecule of interest for insertion into the chosen plasmid, it is preferable to use PCR. Appropriate primers for use in PCR preparation of the sequence can be designed to isolate the required coding region of the nucleic acid molecule, add restriction endonuclease or LIC sites, place the coding region in the desired reading frame.

In a preferred embodiment a nucleic acid molecule for incorporation into an expression vector of the invention, is prepared by the use of the polymerase chain reaction as disclosed by Saiki et al (1988) *Science* 239, 487-491, using appropriate oligonucleotide primers. The coding region is amplified, whilst the primers themselves become incorporated into the amplified sequence product. In a preferred embodiment the amplification primers contain restriction endonuclease recognition sites which allow the amplified sequence product to be cloned into an appropriate vector.

Preferably, the nucleic acid molecule of SEQ ID NO:1 is obtained by PCR and introduced into an expression vector using restriction endonuclease digestion and ligation, a technique which is well known in the art.

Alternatively, the nucleic acid molecule of SEQ ID NO:1 is introduced into an expression vector by yeast homologous recombination (Raymon et al., *Biotechniques.* 26(1): 134-8, 140-1, 1999).

The expression vectors of the invention can contain a single copy of the nucleic acid molecule described previously, or multiple copies of the nucleic acid molecule described previously.

Preferably, the expression vector of the present invention comprises the LuxS coding sequence of SEQ ID NO:1 and the MTA/SAHase encoding gene of SEQ ID NO:3.

Host Cells

"Purified preparation of cells," as used herein, refers to, in the case of cultured cells or microbial cells, a preparation of at least 10%, and more preferably, 50% of the subject cells.

"Ethanologenic cell", as used herein refers to any cell capable producing ethanol. The terms refer to the particular subject cell and also to the progeny or potential progeny of such a cell. Because certain modifications may occur in succeeding generations due to either mutation or environmental influences, such progeny may not, in fact, be identical to the parent cell, but are still included within the scope of the term as used herein.

Another aspect the invention provides an ethanologenic cell for use in the expression system of the present invention which comprises an expression vector, comprising a nucleic acid molecule described herein, e.g. SEQ ID NO:1, or portions or fragments thereof. In an alternative embodiment the cell comprises an expression vector of the present invention, comprising a nucleic acid molecule described herein, e.g., SEQ ID NO:1, or portions or fragments thereof, the vector further comprising sequences which allow it to homologously recombine into a specific site of the cell's genome.

The cell for use in the expression system of the present invention may be an aerobic cell or alternatively a facultative anaerobic cell. Preferably, the cell' is a bacterial cell. Alternatively, the cell may be a yeast cell (e.g. *Saccharomyces, Pichia*), an algae cell, an insect cell, or a plant cell.

Bacterial ethanogenic cells include Gram-positive and Gram-negative bacteria. Suitable bacterial host cells include, but are not limited to the Gram-negative bacteria, for example a bacterium of the family *Zymomonas* most preferably *Zymomonas mobilis*. *Zymoonas mobilis* ZM4 is the most preferred bacterial host cells for the present invention. Expression in *Z. mobilis* offers numerous advantages over other expression systems, particularly as it grows and ferments rapidly, and has a product rate and yield significantly higher than that of yeast. Furthermore, it tolerates high levels of ethanol.

Standard techniques for propagating vectors in prokaryotic hosts are well-known to those of skill in the art (see, for example, Ausubel et al. Short Protocols in Molecular Biology 3rd Edition (John Wiley & Sons 1995)).

To maximize recombinant protein expression in *Z.mobilis*, the expression vectors of the invention may express the nucleic acid molecule incorporated therein in a host bacteria with an impaired capacity to proteolytically cleave the recombinant protein (Gottesman, S., (1990) Gene Expression Technology: Methods in Enzymology 185, Academic Press, San Diego, Calif., 119-128). Alternatively, the nucleic acid molecule incorporated into an expression vector of the invention, can be attenuated so that the individual codons for each amino acid are those preferentially utilized in *Z. mobilis* (Wada et al., (1992) Nucleic Acids Res. 20:2111-2118). Such alteration of nucleic acid sequences of the invention can be carried out by standard DNA synthesis techniques.

Host Cell Transformation

The expression vector of the present invention can be introduced into ethanologenic cells by conventional transformation or transfection techniques.

"Transformation" and "transfection", as used herein, refer to a variety of techniques known in the art for introducing foreign nucleic acids into a ethanologenic cell. Transformation of appropriate cells with an expression vector of the present invention is accomplished by methods known in the art and typically depends on both the type of vector and cell. Said techniques include, but are not limited to calcium phosphate or calcium chloride co-precipitation, DEAE-dextran-mediated transfection, lipofection, chemoporation or electroporation.

Techniques known in the art for the transformation of ethanologenic cells are disclosed in for example, Sambrook et al (1989) Molecular Cloning, A Laboratory Manual, Cold Spring Harbor Laboratory, Cold Spring Harbor, N.Y; Ausubel et al (1987) Current Protocols in Molecular Biology, John Wiley and Sons, Inc., NY; Cohen et al (1972) Proc. Natl. Acad. Sci. USA 69, 2110; Luchansky et al (1988) Mol. Microbiol. 2, 637-646. All such methods are incorporated herein by reference.

Successfully transformed cells, that is, those cells containing the expression vector of the present invention, can be identified by techniques well known in the art. For example, cells transfected with the expression vector of the present invention can be cultured to produce the LuxS protein complex. Cells can be examined for the presence of the expression vector DNA by techniques well known in the art. Alternatively, the presence of the LuxS, or portion and fragments thereof can be detected using antibodies which hybridize thereto.

In a preferred embodiment the invention comprises a culture of transformed ethanologenic cells. Preferably the culture is clonally homogeneous.

The ethanologenic cell can contain a single copy of the expression vector described previously, or alternatively, multiple copies of the expression vector.

Additionally, the ethanologenic cell can be transformed with by genes encoding hydrolases for ethanol production from alternative substrates.

Ethanol Production

Production of ethanol by ethanologenic cells can be up-regulated by exposing said cells to autoinducer molecules. Autoinducer molecules can be supplied to the cell in a culture medium. Autoinducer molecules may be supplied directly to the culture medium. Alternatively, the ethanologenic cells can be co-cultured with an autoinducer producing bacterial cell.

A ethanologenic cell transformed or transfected with an expression vector of the invention, comprising a nucleic acid molecule as described previously, can be used to produce (i.e., express) a ethanol at an increased rate of production relative to a non-transformed or transfected cell.

Preferably, the present invention comprise an expression system for the large scale production of ethonol, utilizing a nucleic acid coding sequence of the present invention, encoding a LuxS protein. Preferably the expression system is an *Z. mobilis* expression system.

Transformed or transfected cells of the invention or ethanologenic cells are grown or cultured in the manner with which the skilled worker is familiar, depending on the host organism. As a rule, ethanologenic cells are grown in a liquid medium comprising a carbon source, usually in the form of sugars, a nitrogen source, usually in the form of organic nitrogen sources such as yeast extract or salts such as ammonium sulfate, trace elements such as salts of iron, manganese and magnesium and, if appropriate, vitamins, at temperatures of between 0° C. and 100° C., preferably between 10° C. and 60° C., while gassing in oxygen.

The pH of the liquid medium can either be kept constant, that is to say regulated during the culturing period, or not. The cultures can be grown batchwise, semi-batchwise or continuously. Nutrients can be provided at the beginning of the fermentation or fed in semi-continuously or continuously. The products produced can be isolated from the organisms as described above by processes known to the skilled worker, for example by extraction, distillation, crystallization, if appropriate precipitation with salt, and/or chromatography. To this end, the host cells can advantageously be disrupted beforehand. In this process, the pH value is advantageously kept between pH 4 and 12, preferably between pH 6 and 9, especially preferably between pH 7 and 8.

An overview of known cultivation methods can be found in the textbook by Chmiel (Bioprozeβtechnik 1. Einführung in die Bioverfahrenstechnik [Bioprocess technology 1. Introduction to Bioprocess technology] (Gustav Fischer Verlag, Stuttgart, 1991)) or in the textbook by Storhas (Bioreaktoren and periphere Einrichtungen [Bioreactors and peripheral equipment] (Vieweg Verlag, Brunswick/Wiesbaden, 1994)).

The culture medium to be used must suitably meet the requirements of the strains in question. Descriptions of culture media for various microorganisms can be found in the textbook "Manual of Methods for General Bacteriology" of the American Society for Bacteriology (Washington D.C., USA, 1981).

As described above, these media which can be employed in accordance with the invention usually comprise one or more carbon sources, nitrogen sources, inorganic salts, vitamins and/or trace elements.

Preferred carbon sources are sugars, such as mono-, di- or polysaccharides. Examples of carbon sources are glucose, fructose, mannose, galactose, ribose, sorbose, ribulose, lactose, maltose, sucrose, raffinose, starch or cellulose. Sugars can also be added to the media via complex compounds such as molasses or other by-products from sugar refining. The addition of mixtures of a variety of carbon sources may also be advantageous. Other possible carbon sources are oils and fats such as, for example, soya oil, sunflower oil, peanut oil and/or coconut fat, fatty acids such as, for example, palmitic acid, stearic acid and/or linoleic acid, alcohols and/or polyalcohols such as, for example, glycerol, methanol and/or ethanol, and/or organic acids such as, for example, acetic acid and/or lactic acid.

Nitrogen sources are usually organic or inorganic nitrogen compounds or materials comprising these compounds. Examples of nitrogen sources comprise ammonia in liquid or gaseous form or ammonium salts such as ammonium sulfate, ammonium chloride, ammonium phosphate, ammonium carbonate or ammonium nitrate, nitrates, urea, amino acids or complex nitrogen sources such as cornsteep liquor, soya meal, soya protein, yeast extract, meat extract and others. The nitrogen sources can be used individually or as a mixture.

Inorganic salt compounds which may be present in the media comprise the chloride, phosphorus and sulfate salts of calcium, magnesium, sodium, cobalt, molybdenum, potassium, manganese, zinc, copper and iron.

Inorganic sulfur-containing compounds such as, for example, sulfates, sulfites, dithionites, tetrathionates, thiosulfates, sulfides, or else organic sulfur compounds such as mercaptans and thiols may be used as sources of sulfur for the production of sulfur-containing fine chemicals, in particular of methionine.

Phosphoric acid, potassium dihydrogenphosphate or dipotassium hydrogenphosphate or the corresponding sodium-containing salts may be used as sources of phosphorus.

Chelating agents may be added to the medium in order to keep the metal ions in solution. Particularly suitable chelating agents comprise dihydroxyphenols such as catechol or protocatechuate and organic acids such as citric acid.

The fermentation media used according to the invention for culturing ethanologenic cells usually also comprise other growth factors such as vitamins or growth promoters, which include, for example, biotin, riboflavin, thiamine, folic acid, nicotinic acid, panthothenate and pyridoxine. Growth factors and salts are frequently derived from complex media components such as yeast extract, molasses, cornsteep liquor and the like. It is moreover possible to add suitable precursors to the culture medium. The exact composition of the media compounds heavily depends on the particular experiment and is decided upon individually for each specific case. Information on the optimization of media can be found in the textbook "Applied Microbiol. Physiology, A Practical Approach" (Editors P. M. Rhodes, P. F. Stanbury, IRL Press (1997) pp. 53-73, ISBN 0 19 963577 3). Growth media can also be obtained from commercial suppliers, for example Standard 1 (Merck) or BHI (brain heart infusion, DIFCO) and the like.

All media components are sterilized, either by heat (20 min at 1.5 bar and 121° C.) or by filter sterilization. The components may be sterilized either together or, if required, separately. All media components may be present at the start of the cultivation or added continuously or batchwise, as desired.

The culture temperature is normally between 15° C. and 45° C., preferably at from 25° C. to 40° C., more preferably at from 25 to 37° C., more preferably from 35 to 37° C., more preferably at 37° C., and may be kept constant or may be altered during the experiment. The pH of the medium should be in the range from 5 to 8.5, preferably around 7.0. The pH for cultivation can be controlled during cultivation by adding basic compounds such as sodium hydroxide, potassium hydroxide, ammonia and aqueous ammonia or acidic compounds such as phosphoric acid or sulfuric acid. Foaming can be controlled by employing antifoams such as, for example, fatty acid polyglycol esters. To maintain the stability of vector it is possible to add to the medium suitable substances having a selective effect, for example antibiotics. Aerobic conditions are maintained by introducing oxygen or oxygen-containing gas mixtures such as, for example, ambient air into the culture. The temperature of the culture is normally 20° C. to 45° C. and preferably 25° C. to 40° C. The culture is continued until formation of the desired product is at a maximum. This aim is normally achieved within 10 to 160 hours.

The fermentation broths obtained in this way, in particular those comprising polyunsaturated fatty acids, usually contain a dry mass of from 7.5 to 25% by weight.

The fermentation broth can then be processed further. The biomass may, according to requirement, be removed completely or partially from the fermentation broth by separation methods such as, for example, centrifugation, filtration, decanting or a combination of these methods or be left completely in said broth. It is advantageous to process the biomass after its separation.

However, the fermentation broth can also be thickened or concentrated without separating the cells, using known methods such as, for example, with the aid of a rotary evaporator, thin-film evaporator, falling-film evaporator, by reverse osmosis or by nanofiltration. Finally, this concentrated fermentation broth can be processed to obtain the fatty acids present therein.

Preferably, transformed or transfected host cells are cultured so that an AI-2 molecule is produced. Preferably, cells are cultured in conditions capable of inducing ethanol production by the host cell.

Preferably, the cells are provided with the necessary substrates for AI-2 production.

Transformed or transfected host cells can be cultured using a batch fermentation, particularly when large scale production of ethanol using the LuxS expression system of the present invention is required. Alternatively, a fed batch and/or continuous culture can be used to generate a yield of ethanol from host cells transformed with the LuxS expression system of the present invention.

Transformed or transfected host cells can be cultured in aerobic or anaerobic conditions. In aerobic conditions, preferably, oxygen is continuously removed from the culture medium, by for example, the addition of reductants or oxygen scavengers, or, by purging the reaction medium with neutral gases.

Techniques known in the art for the large scale culture of host cells are disclosed in for example, Bailey and Ollis (1986) Biochemical Engineering Fundamentals, McGraw-Hill, Singapore; or Shuler (2001) Bioprocess Engineering: Basic Concepts, Prentice Hall. All such techniques are incorporated herein by reference.

The host cells of the invention can be cultured in a vessel, for example a bioreactor. Bioreactors, for example fermentors, are vessels that comprise cells or enzymes and typically are used for the production of molecules on an industrial scale. The molecules can be recombinant proteins (e.g. enzymes such as LuxS) or compounds that are produced by the cells contained in the vessel or via enzyme reactions that are completed in the reaction vessel. Typically, cell based bioreactors comprise the cells of interest and include all the nutrients and/or co-factors necessary to carry out the reactions.

Examples

Increased Ethanol Production

The inventors have demonstrated that Z. mobilis is responsive to the autoinducer molecules from both bacteria and yeast. When E. coli strain KX1123 (Xavier, K B and Bassler, B L (2005) Interference with AI-2-mediated bacterial cell-cell communication. Nature 437, 750-753) was co-cultured with Z. mobilis, from which it was separated by a dialysis bag (with a 10 kDa cut-off) to avoid the toxic effects of bacteriocin production, it stimulated Z. mobilis to overproduce at least 5 proteins, 2 which were retained in the cytoplasm and 3 that were secreted. These proteins were not produced when Z. mobilis was co-cultured with the luxS-deletion strain KX1128, which lacks the LuxS enzyme that is responsible for the synthesis of 4,5-dihydroxy-2,3-pentanedione (DPD) from S-ribosylhomocysteine, which spontaneously cyclizes to form the autoinducer molecule Autoinducer-2 (AI-2). The same Z. mobilis response to co-culture with luxS and luxS-deletion strains of Staphylococcus aureus (9) was also found (Doherty, N et al. (2006) Functional analysis of luxS in Staphylococcus aureus reveals a role in metabolism but not quorum sensing. J Bacteriol. 188, 2885-97).

Purified PufX and LuxS enzymes were used to produce AI-2 in vitro and the results demonstrate the same effect on Z. mobilis, i.e. an over production of the same five proteins. Interestingly, it was found that Z. mobilis was also responsive to DH5α that also lacked the luxS gene, suggestindihat it produces another, as yet unidentified, autoinducer molecule.

A luminescence assay, based upon using Vibrio harveyi BB170 that produces bioluminescence in response to AI-2, to detect AI-2 (Xavier, K B and Bassler, B L (2005) Interference with AI-2-mediated bacterial cell-cell communication. Nature 437, 750-753). A search of the Z. mobilis genome failed to identify a luxS homologue and, using the bioluminescence assay, no AI-2 production was detected by Z. mobilis. Indeed, most, if not all, organisms have a pathway to recycle S-adenosylmethionine (SAM), via S-adenosylhomocysteine (SAH), either using a two-step enzymatic conversion by Pfs and LusX to produce AI-2; or, a one-step conversion using SAH hydrolase. Z. mobilis has a gene that appears to encode a SAH hydrolase, indicating it utilizes this pathway, rather than the Pfs/LuxS pathway that would lead to AI-2 production.

The proteins overproduced in response to AI-2 were identified by mass spectrometry sequencing of tryptic-fragments. The first of the secreted proteins, ZMO1147, was identified as a homologue of the E. coli periplasmic chaperone Skp/HlpA (Walton, T A and Sousa M C (2004) Crystal structure of Skp, a prefoldin-like chaperone that protects soluble and membrane proteins from aggregation. Mol Cell. 15, 367-74). This chaperone works in conjunction with the outer-membrane protein YaeT, which has been shown to be a key component of a complex that is responsible for the insertion of proteins into the outer-membrane (Wu T et al. (2005) Identification of a multicomponent complex required for outer membrane biogenesis in Escherichia coli. Cell 121, 235-45). In E.coli the yaeT and hlpA genes are clustered. In Z. mobilis, ZMO1147 is clearly transcriptionally linked to ZMO1148, a homologue of yaeT, being directly downstream of ZMO1148, so that they share the same promoter. Consequently, both ZMO1147 and ZMO1148 must be induced by AI-2. Considering that members of the YaeT family have homology with the OMP components of type II secretion systems, suggests that ZMO1148 is utilized for the secretion of ZMO1147 and the other proteins induced by AI-2. Clearly, ZMO1147 must have a role above and beyond acting as a periplasmic chaperone. The other two secreted proteins were identified as ZMO1034, with homology to a group of small EF-hand $Ca^{2+}$-binding proteins, and ZMO0994, with homology with to LEA proteins. All the secreted proteins had signal sequences that would suggest they are targeted to the periplasm. We tested the targeting of these proteins expressed in *E. coli* and found that whilst ZMO1147 was retained within the cell, whilst both ZMO1034 and ZMO0994 where excreted. This is an important discovery because it is generally accepted that nonpathogenic strains of *E. coli*, particularly derivatives of K12, do not secrete proteins under routine growth conditions. Such secreted proteins have application as carriers for transgenic proteins to circumnavigate toxicity and other contamination issues, such as the presence of lipopolysaccharides, associated with protein production in *E. coli*.

Figure 2:
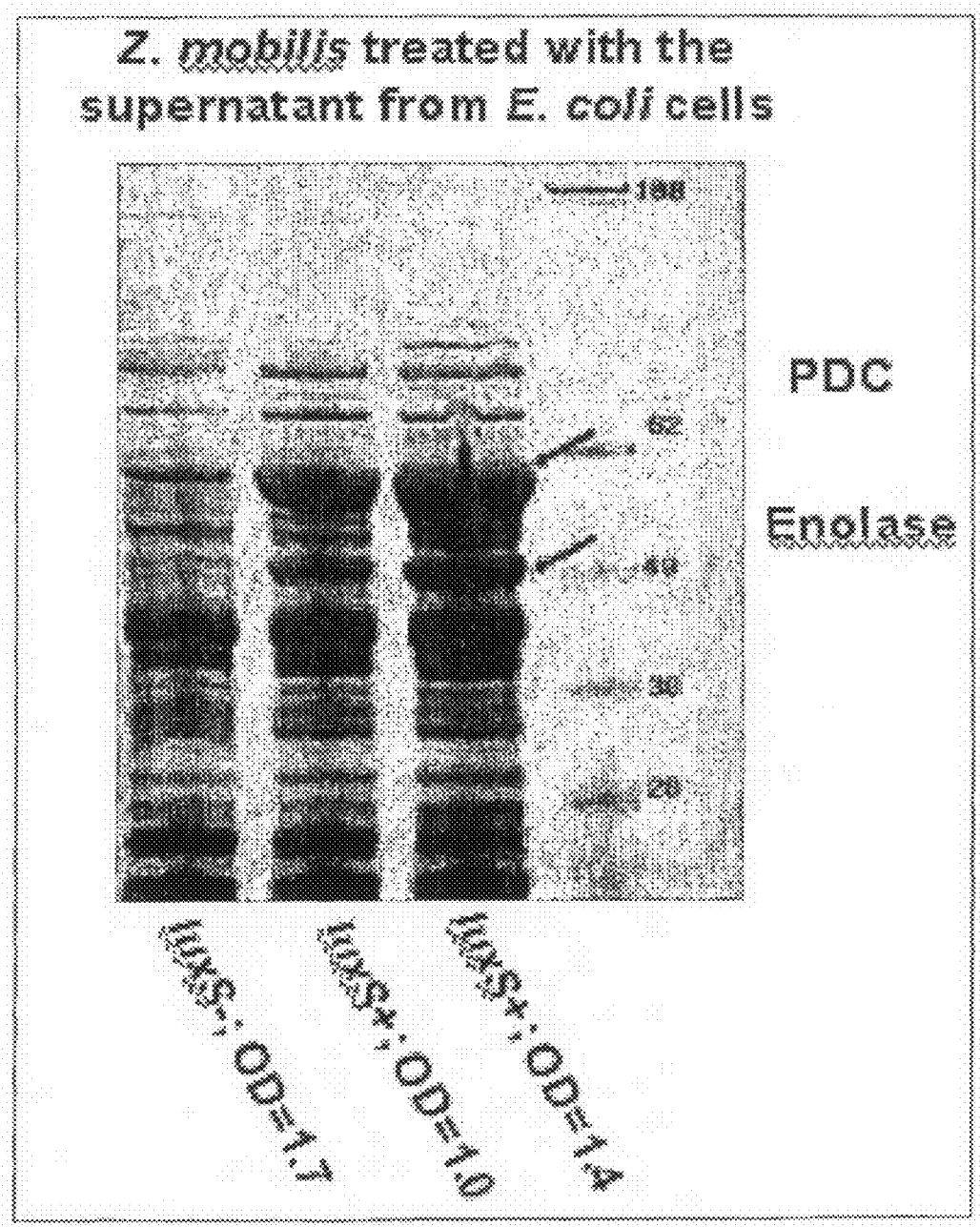
FIG. 2 shows the overproduction of enolase and pyruvate decarboxylase in Z. mobilis treated with supernatants from E. coli.
Figure 3:
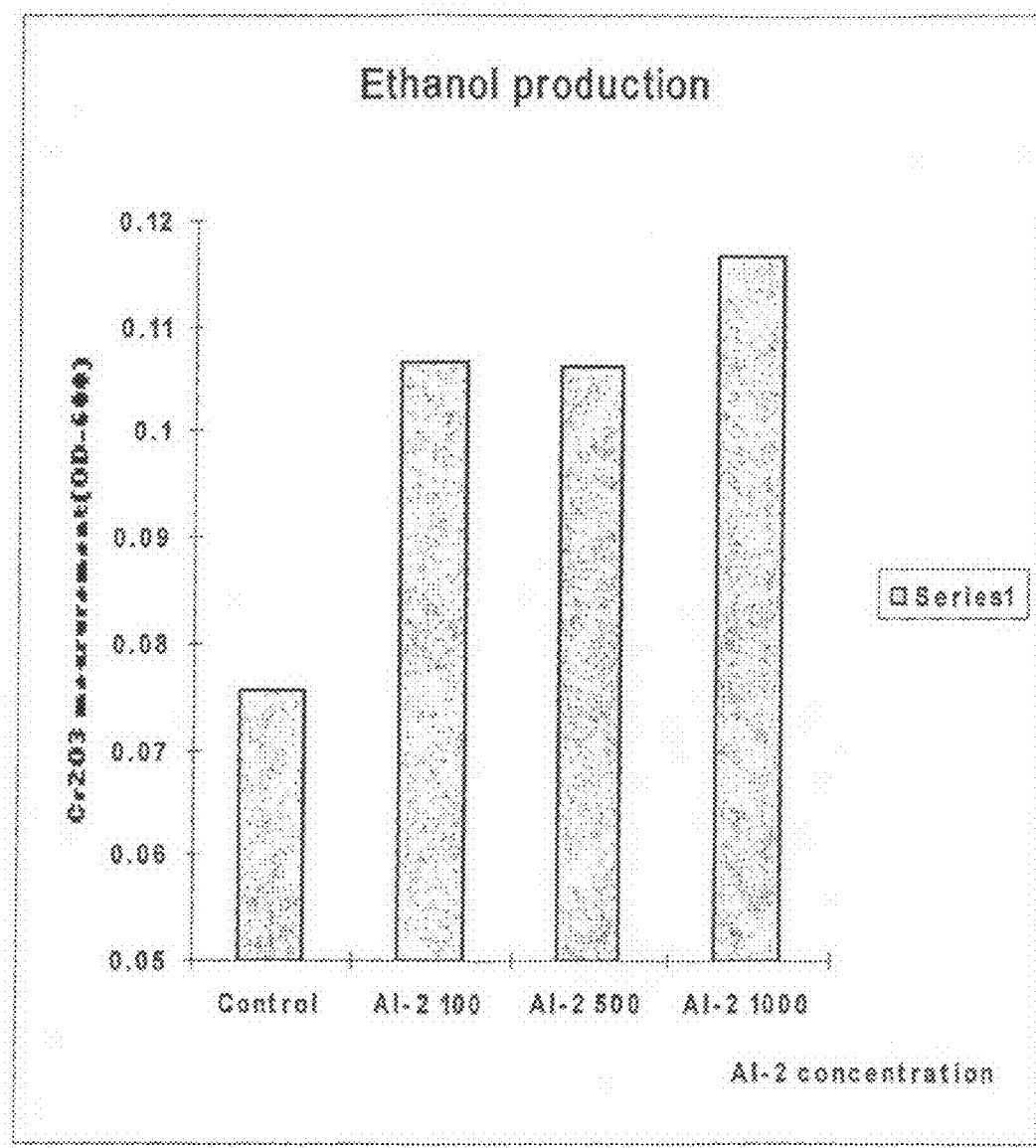
FIG. 3 is a graphical representation showing the increase in ethanol production in AI-2-treated Z. mobilis.

The two overproduced cytosolic proteins were identified as enolase, ZMO1608, and pyruvate decarboxylase, ZMO1360 as illustrated in FIG. 2. These are sequential enzymes in the E-D pathway that leads to ethanol production. Consequently, an assay for ethanol production by untreated and AI-2-treated *Z. mobilis* cells was conducted, establishing that AI-2 treatment leads to a significant increase in ethanol production. A chromate assay (e.g. $3C_2H_5OH+4CrO_3 \rightarrow 2Cr_2O_3+3H_2O$) was used to asses ethanol production, monitoring colour change (e.g. at 600 nm) to determine the ethanol produced. Using this assay, an average 54% increase in ethanol production was observed in two experiments; with the medium ethanol concentration increasing from 9% to 14.2% as illustrated in FIG. 3.

Engineering *Z. mobilis* for AI-2 Production

*Z. mobilis* may be engineered for increased ethanol production by providing the cell with the necessary genetic components for the production of AI-2. For example, the gene for SAH hydrolase, which is used to detoxify SAH may be deleted, and the genes for Pfs and LuxS, which utilise SAH for the production of DPD that spontaneously converts to AI-2, and expressed from a plasmid. Confirmation of AI-2 production may be achieved using the *V. harveyi* bioluminescence assay. AI-2 production may also be confirmed by testing for increased ethanol production.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The invention claimed is:

1. A method for increasing production of ethanol in an ethanologenic cell of the genus *Zymomonas* spp. comprising culturing the ethanologenic cell in the presence of an autoinducer-2 molecule.

2. The method of claim 1, wherein said ethanologenic cell is *Zymomonas mobilis*.

3. The method of claim 2, wherein said ethanologenic cell is *Zymomonas mobilis* ZM4.

4. The method of claim 1, wherein said autoinducer-2 molecule is produced in vitro.

5. The method of claim 1, wherein said autoinducer-2 molecule is provided in a culture medium.

6. The method of claim 1, wherein said autoinducer-2 molecule is provided by co-culturing the ethanologenic cell with an autoinducer-2 molecule-producing bacterial cell.

7. The method of claim 6, wherein said autoinducer-2 molecule-producing bacterial cell is selected from the group consisting of *Vibrio harveyi*, *Escherichia coli*, *Helicobacter pylori*, *Neisseria meningitides*, *Porphyromonas gingivalis*, *Streptococcus pyogenes*, *Shigella flexneri* and *Salmonella typhimurium*.

8. The method of claim 1, wherein the autoinducer-2 molecule is present at the start of culture.

9. The method of claim 1, wherein the autoinducer-2 molecule is present after the start of culture.

10. The method of claim 1, wherein the autoinducer-2 molecule is present continuously during culture.

11. The method of claim 1, wherein the autoinducer-2 molecule is present in the log phase of culture.

12. The method of claim 1, wherein said ethanologenic cell does not synthesize the autoinducer-2 molecule.

* * * * *

UNITED STATES PATENT AND TRADEMARK OFFICE
CERTIFICATE OF CORRECTION

PATENT NO. : 8,163,526 B2  
APPLICATION NO. : 12/446139  
DATED : April 24, 2012  
INVENTOR(S) : Walmsley et al.

Page 1 of 1

It is certified that error appears in the above-identified patent and that said Letters Patent is hereby corrected as shown below:

On the Title Page, Item (56) under OTHER PUBLICATIONS, in Tano et al., replace
        "erthanol" with --ethanol--.

Column 1, Line 33, replace "U$14 billions" with --US $14 billion--.

Column 6, Line 22, replace "an have" with --and have--.

Column 8, Line 29, replace "and it's associated" with --and its associated--.

Column 12, Line 44, replace "SEQ ID NO' 2" with --SEQ ID NO: 2--.

Column 13, Line 53, replace "SEQ ID NO:4or" with --SEQ ID NO: 4 or--.

Column 20, Line 37, replace "suggestindihat" with --suggesting that--.

Signed and Sealed this
Twelfth Day of March, 2013

Teresa Stanek Rea
*Acting Director of the United States Patent and Trademark Office*